US 7,955,645 B2

(12) United States Patent
Mayer et al.

(10) Patent No.: US 7,955,645 B2
(45) Date of Patent: Jun. 7, 2011

(54) METHOD FOR APPLYING SELECTIVELY A LAYER TO A STRUCTURED SUBSTRATE BY THE USAGE OF A TEMPERATURE GRADIENT IN THE SUBSTRATE

(75) Inventors: Felix Mayer, Stäfa (CH); Christoph Kleinlogel, Zurich (CH)

(73) Assignee: Sensirion AG (CH)

( * ) Notice: Subject to any disclaimer, the term of this patent is extended or adjusted under 35 U.S.C. 154(b) by 375 days.

(21) Appl. No.: 11/791,549

(22) PCT Filed: Nov. 23, 2005

(86) PCT No.: PCT/CH2005/000691
§ 371 (c)(1),
(2), (4) Date: May 12, 2009

(87) PCT Pub. No.: WO2006/056090
PCT Pub. Date: Jun. 1, 2006

(65) Prior Publication Data
US 2009/0239371 A1  Sep. 24, 2009

Related U.S. Application Data

(60) Provisional application No. 60/656,501, filed on Feb. 25, 2005.

(30) Foreign Application Priority Data

Nov. 24, 2004  (CH) .................................. 1937/04

(51) Int. Cl.
*B05D 1/26* (2006.01)
*H01L 21/283* (2006.01)
(52) U.S. Cl. ................ 427/229; 427/226; 438/608

(58) Field of Classification Search ............. 427/226, 427/229
See application file for complete search history.

(56) References Cited

U.S. PATENT DOCUMENTS
4,385,937 A  5/1983  Ohmura
(Continued)

FOREIGN PATENT DOCUMENTS
EP  0230976  1/1987
(Continued)

OTHER PUBLICATIONS

Chemische Technik; Band 2: Neue Technolgie; ISBN 3-527-31032-0; Kapitel 9; S. pp. 836-839.
(Continued)

*Primary Examiner* — Frederick J Parker
(74) *Attorney, Agent, or Firm* — Cooper & Dunham LLP

(57) ABSTRACT

A semiconductor wafer (10) is structured such that fine structures (3), such as membranes, bridges or tongues, with a thickness d<<D are formed, wherein D designates the thickness of the semiconductor wafer (10). Then particles of a desired material are applied. A temporal or spatial temperature gradient is generated in the semiconductor wafer (10), e.g. by progressive heating. In such a heating process the fine structures heat up more quickly and become hotter than the remaining wafer because they have a smaller heat capacity per area and cannot carry off heat as quickly. In this manner, the fine structures can be heated to a temperature that allows a sintering of the particles. For coating the semiconductor wafer (10) is brought into a reactor (11). A precursor compound of a metal is provided and fed to the reactor (11), where a reaction takes place during which the metal is transformed to a final compound and is deposited in the form of particles on the semiconductor wafer (10).

21 Claims, 4 Drawing Sheets

U.S. PATENT DOCUMENTS

| | | | |
|---|---|---|---|
| 4,420,385 A | 12/1983 | Hartsough | |
| 5,571,749 A * | 11/1996 | Matsuda et al. | 438/484 |
| 5,821,402 A * | 10/1998 | Okajima et al. | 73/23.2 |
| 5,902,556 A | 5/1999 | Van De Vyver et al. | |
| 6,051,483 A | 4/2000 | Lee et al. | |
| 6,200,674 B1 | 3/2001 | Kumar et al. | |
| 6,331,330 B1 * | 12/2001 | Choy et al. | 427/475 |
| 6,472,244 B1 * | 10/2002 | Ferrari et al. | 438/53 |
| 6,531,412 B2 | 3/2003 | Conti et al. | |
| 6,777,868 B1 * | 8/2004 | Kosaka et al. | 313/495 |
| 6,830,778 B1 * | 12/2004 | Schulz et al. | 427/123 |
| 6,835,417 B2 | 12/2004 | Saenger et al. | |
| 2003/0040130 A1 | 2/2003 | Mayur et al. | |
| 2004/0028809 A1 | 2/2004 | Bein et al. | |
| 2005/0025215 A1 | 2/2005 | Arndt et al. | |
| 2005/0200993 A1 | 9/2005 | Nishikawa et al. | |
| 2005/0220993 A1 | 10/2005 | Sterzel | |

FOREIGN PATENT DOCUMENTS

| | | |
|---|---|---|
| EP | 0230976 | 5/1987 |
| EP | 0421158 | 9/1990 |
| EP | 0795625 | 9/1997 |
| GB | 1498459 | 1/1978 |
| JP | 2002310983 | 10/2002 |
| JP | 2002323473 | 11/2002 |
| WO | WO9519563 | 7/1995 |
| WO | WO2006061103 | 6/2006 |

OTHER PUBLICATIONS

Nguyen Q T Kidder Jr et al., "Hybrid gas-to-particle conversion and chemical vapor deposition for the production of porous alumina films" Preparation and Characterization, Elsevier Sequoia, NL, vol. 410, No. 1-2, May 1, 2002, pp. 42-52, XP004358247, ISSN: 0040-6090, paragraphs 0001!, 0003!; figures 1, 2 abstract.

Sberveglieri G: "Classical and Novel Techniques for the Preparation of SNO2 Thin-Film Gas Sensors" Sensors and Actuators B, Elsevier Sequoia S.A., Lausanne, CH, vol. 6, 1992, pp. 239-247, XP001173062, ISSN: 0925-4005 figure 1.

Majoo S et al.: "A silicon micromachined conductometric gas sensor with a maskless Pt sensing film deposited by selected-area CVD", Sensors and Actuators B, Elsevier Sequoia S.A., Lausanne, CH, vol. 36, No. 1, Oct. 1996, pp. 312-319, XP004061087, ISSN: 0925-4005, abstract; figures 1, 3 paragraph '0002!.

Cavicchi R E et al: "Growth of SNO2 Films on Micromachined Hotplates" Applied-physics letters, AIP American Institute of Physics, Melville, NY, US, vol. 566, No. 7, Feb. 13, 1995, pp. 812-814, XP00489865 ISSN: 0003-6951 the whole document.

* cited by examiner

METHOD FOR APPLYING SELECTIVELY A LAYER TO A STRUCTURED SUBSTRATE BY THE USAGE OF A TEMPERATURE GRADIENT IN THE SUBSTRATE

CROSS REFERENCES TO RELATED APPLICATIONS

This application claims the priority of Swiss patent application 01937/04, filed 24 Nov. 2004, as well as of U.S. provisional application 60/656,501, filed 25 Feb. 2005, the disclosure of both of which is incorporated herein by reference in its entirety.

TECHNICAL FIELD

The invention relates to a method for applying a layer of a material on a substrate, in particular a semiconductor wafer, according to the preamble of the independent claims.

BACKGROUND ART

Applying layers, in particular sintered layers, on semiconductor wafers and other substrates is of interest for a plurality of applications. For example, substance sensors requiring a sintered layer of $SnO_2$ as active layer are known. It has been found, however, that it is not easy to carry out a suited sintering process on a semiconductor wafer. In particular, circuits etc. integrated in the wafer can be damaged during sintering.

DISCLOSURE OF THE INVENTION

Hence it is an object to provide a method of this type that allows efficient manufacturing of such layers. This object is achieved by the independent claims.

In a first aspect of the invention the substrate is being structured, namely in such manner that fine structures, such as membranes, bridges, tongues or porous regions having a thickness $d \ll D$ are formed (advantageously by means of removing material), wherein D designates the thickness of the substrate. Then particles of the desired material are deposited and a temporal or spatial temperature gradient is created within the substrate before, during or after depositing the particles, namely in such a way that the fine structures reach a higher temperature than the rest of the substrate. The term "temporal temperature gradient" is used to express that the temperature changes in time.

For example, the substrate is increasingly heated for this purpose, e.g. by irradiation or by bombardment by hot material from the outside. In such a heating process, fine structures are being heated more quickly and become hotter than the rest of the substrate since they have a smaller heat capacity per area and cannot carry off heat as easily. In this manner, the fine structures can be heated to a temperature T that allows an efficient deposition and, where applicable, a sintering of the particles, while the temperature T' in the rest of the substrate remains lower. This offers, on the one hand, the possibility to deposit or sinter particles depending on the position on the substrate, e.g. only in the region of the fine structures but not on the remaining regions of the substrate. On the other hand, it allows to use higher deposition or sintering temperatures at which the electronic circuits e.g. located in other regions of the substrate would be damaged.

The term "structured regions" is, in the following, being used for those regions of the substrate where there are thermally insulated structures of said thickness $d \ll D$, while the term "unstructured regions" designates those regions where no such structures are present.

The structures advantageously comprise at least two free surfaces, the distance between which corresponds at most to the thickness d. "Free surfaces" is to be understood as designating surfaces in the thermal sense, i.e. the free surfaces abut against a medium that has a thermal conductivity and heat capacity much smaller that the one of the used semiconductor. The medium is advantageously gas or vacuum. For such structures, the heat loss while heating is small such that they become hot quickly.

In a second aspect of the invention a layer, advantageously a structured layer, of a material on a substrate is manufactured by introducing the semiconductor layer into a reactor. A precursor compound of a metal is provided and fed to the reactor. Furthermore, a substance Y is fed to the reactor. A chemical reaction takes place in the reactor, during which the metal is transformed to a final compound and is deposited on the substrate in the form of particles.

This procedure allows the direct coating of a substrate with particles of the desired final compound.

The reaction for transforming the metal to the final compound can take place on the substrate, e.g. if the precursor (e.g. in dissolved state) is deposited on the substrate and then reacts with the substance Y. The reaction can, however, also take place prior to deposition if the precursor reacts with the substance Y prior to hitting the substrate, whereupon the final compound is formed, which then hits the substrate e.g. in solid form or as droplets.

Advantageously, the substance Y comprises oxygen or nitrogen and the final compound comprises an oxide and/or nitride compound of the metal.

The metal can be a pure metal or a mixture of several metals.

Advantageously a flame synthesis takes place in the reactor.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

At first, a preferred embodiment of the invention is described for the example of a substance sensor. In a second part of the description, advantageous further embodiments are then shown.

Figure 1:
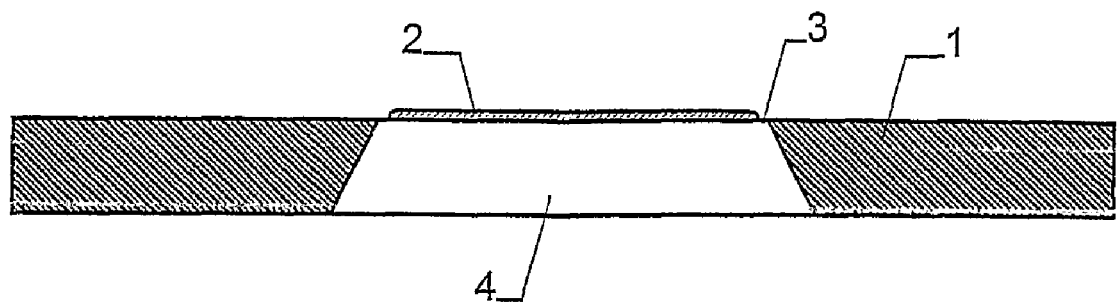
FIG. 1 a sectional view of a substance sensor with a measuring layer of tin oxide ceramics, FIG. 2 the schematic representation of a first embodiment of the coating method, FIG. 3 the schematic representation of a second embodiment of the coating method, and FIG. 4 the schematic representation of a third embodiment of the coating method.

FIG. 1 shows a substance sensor with a semiconductor substrate 1 and a measuring layer 2. The measuring layer 2 is arranged on a thin membrane 3 or bridge, which spans an opening 4 in the semiconductor substrate 1, on the top side of the substrate. The opening 4 extends through the substrate 1 to its bottom side. A heating is arranged in membrane 3, by means of which the measuring layer 2 can be heated to approximately 200-400° C., as well as two electrodes, by means of which the electrical resistance of the measuring layer can be determined. Arranging the measuring layer 3 on the membrane has the advantage that the desired operating temperature can be reached with comparatively low electrical power.

A sensor of the type shown in FIG. 1 is known, per se, to the person skilled in the art. It is based on the principle that the electric resistance of measuring layer 2 changes under the influence of certain gases, such as CO, $CO_2$ or carbohydrates.

Measuring layer 3 consists e.g. of ceramics of tin oxide ($SnO_2$) with contributions of magnesium oxide or other additions or dopants, such as platinum and/or palladium. It should be porous for being sufficiently sensitive.

Evaluation electronics can be integrated on semiconductor substrate 1, which electronics carry out at least a preprocessing or a complete processing up to digitization of the measured resistance values.

In the following, a procedure for manufacturing such devices is described.

As usual in semiconductor technology, the sensor of FIG. 1 is manufactured together with a plurality of further, identical sensors on a semiconductor wafer.

Figure 2:
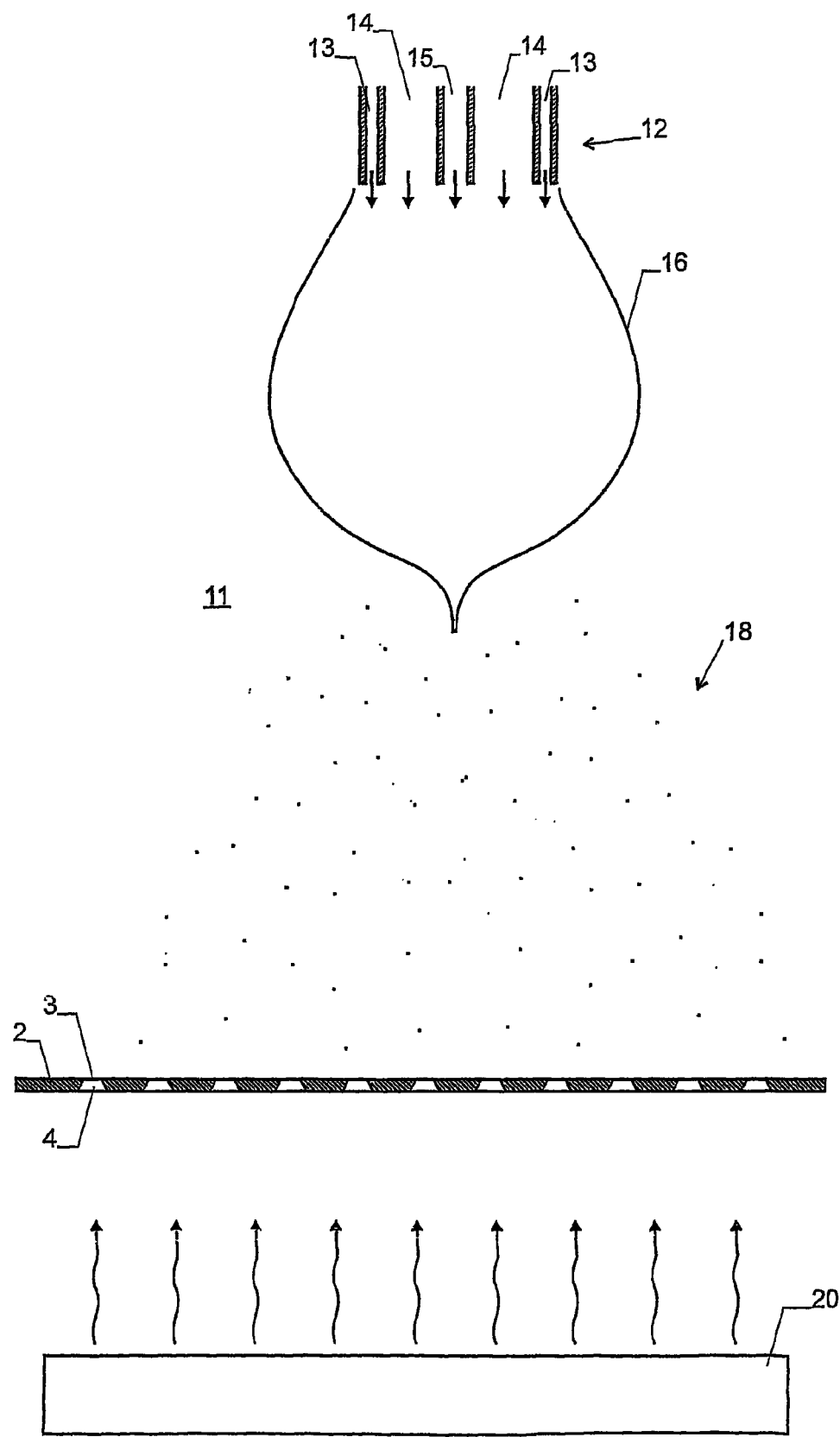

For this purpose, a semiconductor wafer 10, as it is shown in FIG. 2, is first processed by means of conventional procedures. In particular, a plurality of membranes 3 or other fine structures, such as webs or bridges, are manufactured on the top side of the wafer. The fine structures or membranes 3 are arranged over openings 4, which extend through semiconductor wafer 10 to its bottom side.

For manufacturing the membranes 3, one or more coatings of e.g. silicon oxide or silicone nitride, combined, if necessary, with conducting layers, are applied, in per se known manner, to the top side of the wafer, and then the wafer is etched off anisotropically from the bottom side in the region of the openings 4, such that the coatings remain and form the membranes 2. Furthermore, advantageously, the further required components are also integrated on the top side of semiconductor wafer 10, such as electrodes for contacting the measuring layer 2, conductors, contact pads and, where applicable, processing electronics, advantageously in CMOS technology.

The semiconductor wafer 10 manufactured in this way therefore comprises structured regions (namely the membranes 3) with a thickness d between e.g. 1 and 50 μm, while, otherwise, the thickness of the wafer is e.g. some 100 μm.

In a next step the measuring layer 2 is applied. For this purpose the semiconductor wafer 10 structured in the previous step is introduced into a reactor 11, as it is e.g. shown in FIG. 2.

An apparatus 12 for carrying out flame synthesis or flame pyrolysis is arranged in reactor 11. It consists e.g. of several concentric tubes 13-15. An inflammable gas is introduced through an outer tube 13. A dispersion gas is introduced through a next inner tube 14 and a precursor compound is introduced through an innermost tube 15.

The precursor compound is e.g. a compound that comprises the metal for the coating, such as $SnCl_4$ or an organometallic compound. The precursor compound can, if it is liquid of gaseous, be provided directly. It can, however, also be provided as a solution. Both variants are possible for $SnCl_4$. Advantageously the precursor compound is fed to the reactor in the form of a suspension.

The dispersion gas can e.g. comprise oxygen, or also be an inert gas. The dispersion gas serves to nebulize the precursor compound.

The inflammable gas from tube 13 is ignited such that a flame 16 is formed. In this flame the precursor compound is transformed to a final compound, in the present case tin oxide ($SnO_2$) by reaction with oxygen. The oxygen can originate, as mentioned above, from the dispersion gas or be fed separately, e.g. through tube 13 together with the inflammable gas, or through a separate feed.

The final compound forms droplets or particles 18, which are deposited on semiconductor wafer 10.

At the same time the wafer 10 is subjected to a temporal temperature gradient by being heated by flame 16 and/or another heat source, such as an infrared lamp 20, from the outside and changing its temperature in time-dependent manner. During this, the thin structures of the wafer 10, i.e. the membranes 3, are heating up much faster than the thick regions. For example, a temperature T of e.g. above 600° C. can in this way be reached in the region of the membranes 3, while the temperature T' at the top side of the thick regions does not yet exceed 200° C. In this manner, the particles 18 can e.g. be subjected to a temperature sufficient for sintering or adhesion in the region of membrane 3, but not outside the membranes 3. The heat sources are switched of or reduced in power before the top side of the thick regions reaches as high temperatures as the thin regions of the semiconductor wafer.

By means of this procedure, an adhesion or even sintering of the particles 18 is achieved in the region of the thin structures, while the particles hitting the thick regions of the wafer adhere and are sintered only weakly or not at all.

In a next step the semiconductor wafer 10 can be removed form reactor 11. The excessive particles on the thick regions of the wafer are, if necessary, removed, e.g. by washing.

Figure 3:
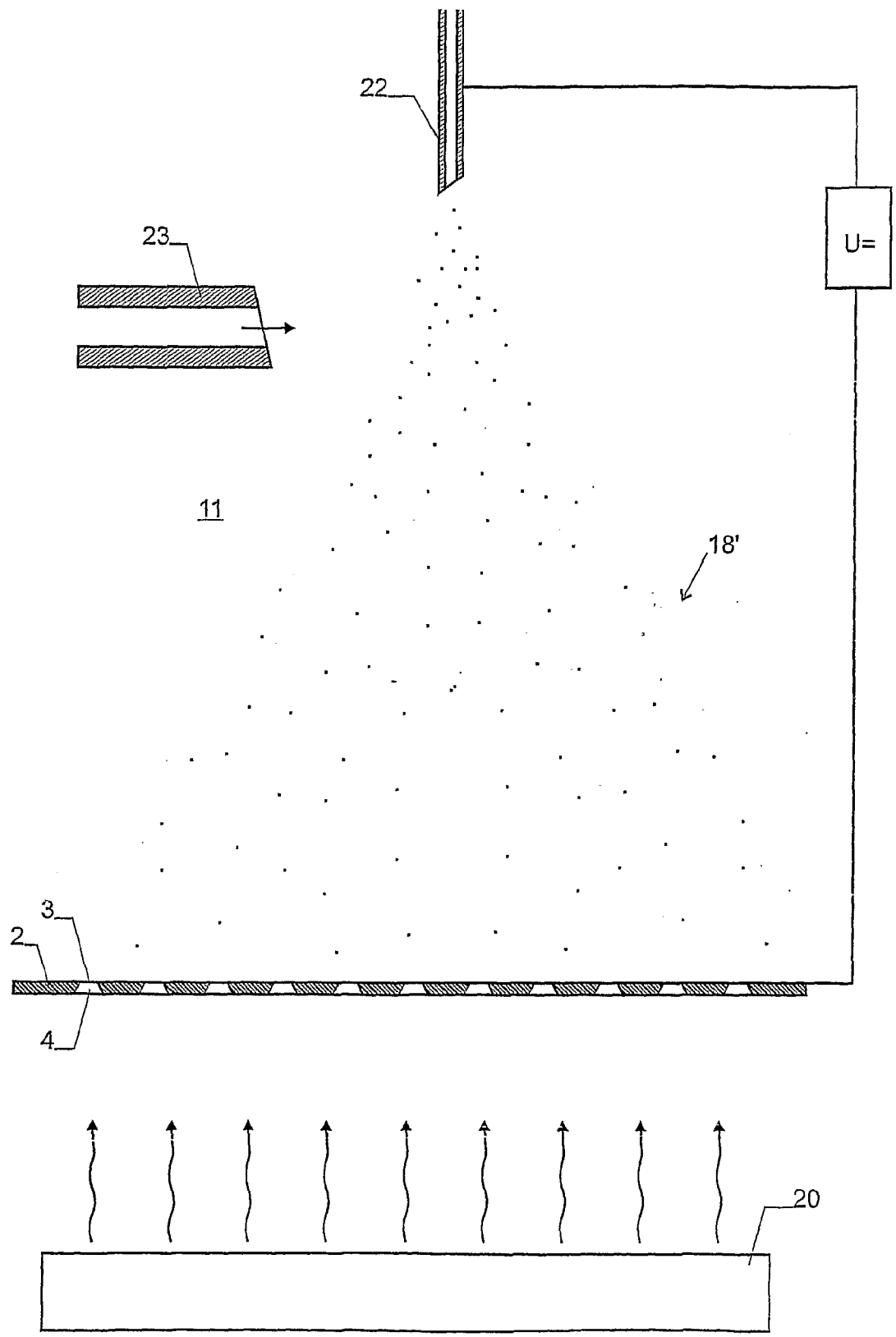

An alternative coating procedure is shown in FIG. 3. Also in this case, the semiconductor wafer 10 is first structured and then introduced into a reactor 11. In reactor 11, a nebulizer 22 is provided, by means of which the precursor material is nebulized and applied as droplets 18' to a first side of the semiconductor wafer 10. At the same time, a reaction substance Y, such as oxygen, is fed to the reactor through a further nozzle 23.

The semiconductor wafer is irradiated from a second side by means of a infrared heat source 20 and thereby subjected to a temporal temperature gradient such that the thin structures or membranes 3 are heating up more quickly than the thick regions of the wafer 10. This procedure is time controlled in such a way that, during the arrival of the particles 18', the thin structures have a substantially higher temperature than the topside of the thick regions of the wafer 10.

In particular in the hot regions a reaction between the reaction gas Y, e.g. oxygen, and the precursor material, which e.g. again comprises $SnCl_4$, takes place, such that tin oxide in the form of more or less solid particles is formed. The temperature in the thin structures is advantageously adjusted such that the particles sinter to each other at the same time.

Also in this case, the process is stopped before the temperature in the thicker regions of wafer 10 becomes too high. Then wafer 10 is taken out of reactor 11 and the excessive particles are removed.

Instead of the two said procedures, other methods can be used for generating particles, e.g. a laser pyrolysis procedure as described in U.S. Pat. No. 6,200,674.

To heat up semiconductor wafer 10, the heat content of the particles 18 or droplets 18' can be used in addition to or instead of heat source 20 if the amount and temperature of the particles 18 or droplets 18' is sufficient for this purpose. Heat can also be fed to the semiconductor wafer, additionally, or alternatively, by means of a hot gas, plasma, ion bombardment or by other means, e.g. by means of the flame 16 of the embodiment of FIG. 2.

By subjecting the semiconductor safer 10 to a temporal temperature gradient, e.g. by continuously increasing its temperature by feeding thermal energy from the outside, higher temperatures are reached in the region of the fine structures or membranes 3 of the embodiments described above than in the other regions of the wafer. Specifically this is achieved by supplying the thermal energy via the surface of waver 10 into the same, e.g. by means of electromagnetic radiation of by bombardment with hot or energy rich particles, molecules, atoms or ions. With this, the fine structures at the surface of the wafer 10 can be heated easily because of their low mass and, at the same time, the heat is not carried of well because of the low thickness of the structures.

Figure 4:
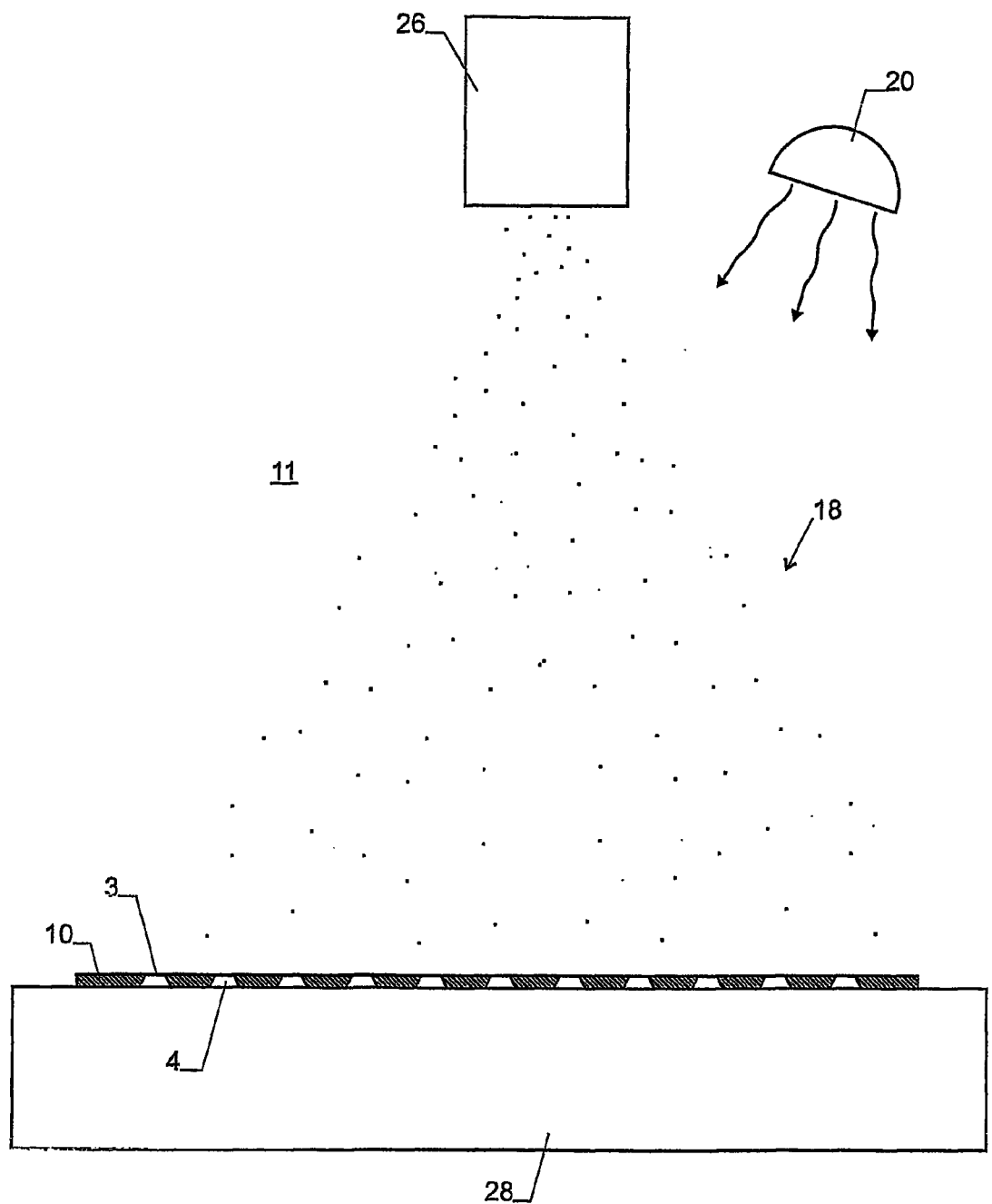

Alternatively or in addition to using a temporal temperature gradient, a local increase of the temperatures in the fine structures can also be achieved in temporal equilibrium with only spatial temperature gradients, as it is schematically shown in FIG. 4. Here, again, a particle source 26 is provided, which is e.g. formed by a flame synthesis apparatus 12 according to FIG. 2, a nebulizer 22 with subsequent chemical transformation according to FIG. 3, or a laser pyrolysis apparatus according to U.S. Pat. No. 6,200,674. The product of the particle source 26 is deposited on the top side of semiconductor wafer 10. At the same time, semiconductor 10 is heated by a heating device 20 e.g. by means of electromagnetic radiation, namely advantageously from the side at which deposition takes place. Semiconductor wafer 10 is placed on a cooled table 28 with its bottom side. With the exception of the regions of the openings 4, semiconductor wafer 10 is in thermal contact with table 28. This arrangement leads to a higher temperature in the region of the fine structures or membranes 3 than in the remaining regions of the wafer, even if the arrangement is in temporal equilibrium.

Hence, a local heating of the fine structures or membranes 3 can also be achieved if only a temporal temperature gradient is generated in semiconductor wafer 10, especially if the heat is carried off from the wafer by bringing it in contact with a cooling device (e.g. table 28). For a strong effect it should be observed that the fine structures or membranes 3 are not in direct contact with the cooling device.

To heat the fine structures or membranes 3, it is also possible to provide heaters in the form of integrated thin conductive strips, which carry a current from an external current source during sintering.

Furthermore, the side of semiconductor wafer 10 facing the particle source 26 can be provided with a mask that makes a deposition of particles outside the desired regions more difficult.

On the other hand, semiconductor 10 can be provided with a coating, in particular in the region of the fine structures or membranes 3, which promotes the deposition of the particles. For example, a material can be used for this purpose that exceeds its glass temperature at the temperatures reigning during deposition or sintering and becomes soft or liquid and enters a close bond with the deposited material.

Tin oxide has been named in the above embodiments as a final compound or material for the particles. Depending on application, however, a plurality of further materials can be used, such as magnesium oxide, aluminum oxide, cerium oxide or zircon oxide, i.e. advantageously oxygen compounds of a metal. Other metal compounds, however, can be used as well, such as nitride compounds. Nonmetallic compounds are possible, too.

In the methods mentioned above a precursor compound is converted to a final compound in reactor 11. The precursor compound can e.g. be a chloride, nitride and or fluoride compound of a metal, such as $SnCl_4$, $SnCl_2$ or $MgCl_2$ or $MgF_2$ or an organometallic compound. The reaction for converting the metal compound into the final compound can either take place before arrival of the precursor compound on the semiconductor wafer 10 or afterwards.

For producing acentric ceramics that e.g. have piezoelectric properties, pyroelectric properties, nonlinear optical properties of second order, or other properties that require a macroscopic acentricity of the ceramics, the ceramics can be polarized by means of an electric or magnetic field during deposition or sintering, e.g. by using the arrangement of FIG. 3. Acentric, piezoelectric ceramics can e.g. be used to integrate SAW filters or piezoelectric actuators on semiconductor wafer 10.

The particles used in the present case are advantageously nanoparticles with diameters smaller than 100 nm, in particular smaller than 10 nm, such that they can take advantage of the melting point reduction that is observed for small particles.

Semiconductor wafer 10 is advantageously a silicon wafer, but other semiconductor materials can be used as well.

The invention is especially suited for manufacturing substance sensors with measuring layers of metal oxide ceramics, e.g. for the detection of nitrogen oxides, carbohydrates, carbon monoxide, or carbon dioxide. As mentioned, it is also possible to manufacture devices with piezoelectric ceramics. Further applications are e.g. the integration of chemically active structures (e.g. catalytic structures) on semiconductor substrates.

The deposited material can be a pure substance, a doped substance of a mixture of several substances.

As mentioned, the deposited material can be sintered. It is also possible to vary the degree of sintering over the deposited layer thickness, e.g. by first depositing at higher temperature for improved adhesion with the substrate such that the bottommost layer is sintered strongly, while the degree of sintering decreases for higher layers.

It is also possible to deposit several layers of coatings, which e.g. differ in their degree of sintering, doping and/or composition.

It is also possible to use, as fine structures in semiconductor wafer 10, needles, hole structures with thin separating walls or porous regions in or on semiconductor wafer 10 instead of membranes, bridges and webs.

The coating can, as mentioned, be structured by choosing the parameters of the process such that the particles only are deposited in the hot regions (i.e. in the region of the fine structures) of the semiconductor wafer 10. It is, however, as mentioned, also possible to achieve a structuring by means of a mask alone, which is applied to semiconductor wafer 10 prior to coating and which hinders or promotes depositing in certain regions. Finally, it is also possible to use a combination of both structuring methods.

The present invention, though especially suited for semiconductor wafers, can be applied for depositing layers on other types of substrates, such as ceramics or glasses.

While there are shown and described presently preferred embodiments of the invention, it is to be distinctly understood that the invention is not limited thereto but may be otherwise variously embodied and practiced within the scope of the following claims.

The invention claimed is:

1. A method for applying a structured layer of a material on a substrate having a thickness D, comprising:
    forming structures of a thickness d in or on the substrate, wherein d is less than D, and
    applying particles of the material to said substrate and heating the substrate for generating a spatial or temporal temperature gradient in the substrate such that the structures reach a higher temperature T than non-structured regions of the substrate, wherein the material is synthesized in a flame during a flame pyrolysis process and the substrate is heated by said flame.

2. The method of claim 1 wherein the particles are sintered at the temperature T.

3. The method of claim 2 wherein a temperature T' in a region of non-structured regions of the substrate remains smaller than a sintering temperature of the particles.

4. The method of claim 1 wherein each structure comprises at least two free surfaces a distance between which corresponds at most to the thickness d.

5. The method of claim 1 wherein the structures are arranged at openings extending through the substrate.

6. The method of claim 1 wherein said structures are membranes, tongues or bridges.

7. The method of claim 1 wherein the substrate is heated by means of electromagnetic radiation.

8. The method of claim 1 wherein the particles are applied from a first side to the substrate, and the substrate is heated from a second side opposite the first side.

9. The method of claim 1 wherein a temporal temperature gradient is generated within the substrate by changing the temperature of the substrate.

10. The method of claim 1 wherein the substrate is provided with a coating in the region of the structures, which coating allows for a deposition of the particles at a temperature reigning during deposition and/or that the substrate is provided with a coating outside the structures, which coating hinders a deposition of the particles.

11. The method of claim 1 wherein the particles have a diameter of not more than 100 nm, in particular not more than 10 nm.

12. The method of claim 1 wherein the layer on the substrate is at least partially polarized by applying an electric or magnetic field.

13. The method of claim 1 wherein the substrate comprises integrated heaters, which are heated during deposition, and in particular wherein the integrated heaters are arranged in or at the structures.

14. The method of claim 1 wherein the substrate is heated by means of heated particles and/or by means of a gas and/or plasma and/or a flame.

15. The method of claim 1 wherein the substrate is brought into contact with a cooling device.

16. The method of claim 1 wherein said substrate is a semiconductor wafer.

17. The method of claim 1 further comprising the step of manufacturing one or more sensors, in particular substance sensors, from said substrate.

18. The method of claim 1 comprising the step of applying a mask over said substrate for structuring said layer.

19. The method of claim 1 comprising the steps of applying several layers on said substrate.

20. A method for applying a structured layer of a material on a substrate having a thickness D, comprising:
    forming structures of a thickness d in or on the substrate, wherein d is less than D, and
    applying particles of the material to said substrate and heating the substrate for generating a spatial or temporal temperature gradient in the substrate such that the structures reach a higher temperature T than non-structured regions of the substrate, wherein the substrate is brought into contact with a cooling device, wherein, the structures are not in direct contact with the cooling device.

21. The method of claim 20 wherein the structures on a first side of the substrate are arranged over openings and the openings extend to a second side of the substrate, wherein the second side of the substrate is brought into contact with the cooling device.

* * * * *